(12) United States Patent
Maass et al.

(10) Patent No.: US 6,440,742 B1
(45) Date of Patent: Aug. 27, 2002

(54) RECOMBINANT AAV VECTOR-BASED TRANSDUCTION SYSTEM AND USE OF SAME

(75) Inventors: Gerd Maass, Sindelsdorf; Christoph Bogedain, Munich; Michael Hallek, Schondorf; Clemens Wendtner; Doris Michl, both of Munich, all of (DE)

(73) Assignee: Medigene, AG, Martinsried (DE)

( * ) Notice: Subject to any disclaimer, the term of this patent is extended or adjusted under 35 U.S.C. 154(b) by 0 days.

(21) Appl. No.: 09/773,302

(22) Filed: Jan. 30, 2001

Related U.S. Application Data

(63) Continuation of application No. 09/142,289, filed on May 5, 1999, now Pat. No. 6,207,453.

(30) Foreign Application Priority Data

Mar. 6, 1996 (DE) .......... 196 08 753
Mar. 6, 1997 (WO) .......... PCT/DE97/00447

(51) Int. Cl.[7] .......... C12N 15/85; C12N 15/63; C07H 21/04; C07K 14/075
(52) U.S. Cl. .......... 435/455; 435/320.1; 536/23.1; 536/24.1; 530/300
(58) Field of Search .......... 435/455, 320.1, 435/235.1; 536/23.1, 24.1; 530/350, 388.21

(56) References Cited

PUBLICATIONS

Paulus Behring Inst Mitt 78:118–132 Dec. 1985.*
Wagner et al. PNAS USA 89:6099–6103 Jul. 1992.*
Weitzman et al. PNAS USA 91:5808–5812 Jun. 1994.*
Chiorini et al. Journal of Virology 68(11):7448–7457 Nov. 1994.*
Anderson Nature 392(Suppl):25–30 Apr. 1998.*
Palu et al. Journal of Biotechnology 68:1–13 1999.*
Verma et al. Nature 389:239–242 Sep. 1997.*

* cited by examiner

*Primary Examiner*—Remy Yucel
*Assistant Examiner*—Katharine F Davis
(74) *Attorney, Agent, or Firm*—Albert P. Halluin; Viola T. Kung; Howrey Simon Arnold & White, LLP

(57) ABSTRACT

The present invention relates to a transduction system, comprising (a) a rep-negative AAV vector containing a foreign DNA and (b) a product providing an AAV Rep protein. The invention also relates to the use of the transduction system.

7 Claims, No Drawings

RECOMBINANT AAV VECTOR-BASED TRANSDUCTION SYSTEM AND USE OF SAME

This application is a continuation of U.S. application Ser. No. 09/142,289, filed May 5, 1999, now U.S. Pat. No. 6,207,453.

FIELD OF THE INVENTION

The present invention relates to a transduction system which comprises a rep-negative AAV vector and its use.

BACKGROUND OF THE INVENTION

The transfer of genes by means of viruses as a vector is referred to as transduction. Transduction is frequently used to integrate genes into the genome of cells. For example, adeno-associated viruses (AAVs) are used as viruses for this purpose.

AAVs are single-stranded DNA viruses belonging to the Parvorirus family. AAVs require helper viruses, particularly adenoviruses or herpesviruses, for their replication. In the absence of helper viruses AAVs integrate into the host cell genome, particularly at a specific site on chromosome 19.

The genome of AAVs is linear and has a length of about 4680 nucleotides. It comprises two reading frames which code for a structural gene and a non-structural gene. The structural gene is referred to as cap gene. It is controlled by the P40 promoter and codes for three capsid proteins. The non-structural gene is referred to as the rep gene and codes for the rep proteins, Rep 78, Rep 68, Rep 52 and Rep 40. The two former proteins are expressed under the control of the P5 promoter while the expression of Rep 52 and Rep 40 is controlled by the P19 promoter. The functions of the Rep proteins are represented inter alia by the control of replication and transcription of the AAV genome.

It has now been determined that recombinant AAVs, i.e., AAVs containing foreign DNA, often do not integrate into the genome of cells, so that the foreign DNA is not transferred either. However, the latter is important and largely indispensable for manipulating cells, particularly for gene therapy.

It is an object of the present invention to provide a product by which a foreign DNA can be integrated into the genome of cells in an effective manner. According to the invention, this is achieved by the subject matter defined in the claims.

BRIEF SUMMARY OF THE INVENTION

Thus, the present invention provides a transduction system, comprising:
(a) a rep-negative AAV vector containing a foreign DNA, and
(b) a product providing an AAV Rep protein.

DETAILED DESCRIPTION OF THE INVENTION

The present invention is based on the discovery that AAVs lacking a rep gene do not integrate into the genome of cells.

The term "rep-negative AAV vector" relates to any AAV, i.e., virus particle, and the DNA thereof, which are rep-negative. This means that no rep gene or only a defective rep gene is present. Conventional methods can be used for providing a rep-negative AAV vector. For example, an AAV DNA can be modified by specific mutagenesis in the rep gene such that it becomes defective or the rep gene is deleted by special restriction cleavage and ligation. A rep-negative AAV DNA can then be transferred into cells which express an AAV-rep gene, and rep-negative AAVs, i.e., virus particules, are obtained after infection with a helper virus.

The term "foreign DNA" includes any DNA that can be integrated into a rep-negative AAV vector. The foreign DNA may be non-coding or coding. In the case of non-coding DNA, the foreign DNA can be a regulator element of the DNA replication and/or transcription. In the case of coding DNA, it is preferable for the foreign DNA to be expressible. It is especially preferred that the expression be controlled by an inducible promoter such as a tissue-specific promoter. In addition, the foreign DNA can code for a diagnostic and/or therapeutic protein. Examples of therapeutic proteins include tumor necrosis factor, interferons, interleukins, lymphokines, growth factors, plasma proteins and receptors. In addition, the foreign DNA can be inserted at any site on the rep-negative AAV vector. It may be advantageous for the foreign DNA to be present in or in place of the rep gene. Furthermore, in some embodiments, several foreign DNAs are present.

The term "a product providing an AAV-Rep protein" includes any product which can provide an AAV Rep protein, particularly Rep 78 or Rep 68, or a portion thereof. For example, the product may be a DNA (rep-DNA) adapted to express an AAV Rep protein and a portion thereof, respectively. It is preferable for the expression of the rep-DNA to be controlled by an inducible promoter such as an antibiotic-specific or tissue-specific promoter. The rep-DNA may be provided by the genome of an AAV virus particle. It is preferable for the genome to have a defective (deleted) cap gene and an inducible promoter for the cap gene, respectively, and/or one or more defective (deleted) ITR sequences. The genome and the corresponding AAV virus particle may also be a product within the meaning of the term. In addition, the product may be an AAV Rep protein, particularly Rep 78 or Rep 68, or a portion thereof and a fusion protein that contains an AAV Rep protein or a portion thereof. Such proteins can be provided by conventional methods.

Components (a) and (b) may be connected with each other in a transduction system according to the present invention. Such a connection may be made by conventional methods. For example, if the AAV vector of component (a) is present as a virus particle and the product of component (b) is available as rep-expressing DNA, it may be preferred to proceed in the following manner: The AAV vector may be modified chemically or enzymatically. For example, it may be biotinylated, i.e., biotin or a biotinylated anti-AAV antibody such as an antibody directed against the AAV proteins VP-1, VP-2 or VP-3 may be bound to an AAV vector. The rep-expressing DNA may be mixed with DNA-binding substances such as organic polycations, e.g., polylysine and/or polyornithine, and heterologous polycations having several differing, positively charged amino acids, respectively.

It is especially preferred to mix the rep-expressing DNA with polylysine and streptavidin so that polylysine binds to the DNA and streptavidine binds to the polylysine. The biotinylated AAV vector and the streptavidine-polylysine-modified DNA are then mixed, so that the bond between components (a) and (b) is formed.

Such a transduction system is suitable for the transduction of cells. The cells may be of any type or origin. Furthermore, the cells may be present separately or in aggregation such as in a tissue or an organ. The cells may also be present within or outside an organism. In the latter case, the cells may be held in culture. Moreover, the cells may be healthy cells, diseased cells such as virus-infected cells or cells affected by microorganisms or protozoa, or tumor cells.

The cells may be transduced by common methods. If a transduction system is used wherein components (a) and (b) are connected with each other and the AAV vector and/or the product is present as a virus particle, the cells can be infected with the transduction system. However, if the AAV vector and the product are present as DNA, the transduction system can be introduced into the cells, e.g., by transfection, lipofection or electroporation.

If a transduction system is used wherein components (a) and (b) are not connected with each other, and the AAV vector and the product are present as a virus particle, the cells can be infected with the virus particles. However, if the AAV vector is present as a virus particle and the product as DNA or vice versa, the cells may be infected with the AAV vector and the product. The DNA can be introduced into the cells as described above.

Furthermore, if the AAV vector and the product are each present as DNA, they can be introduced into the cells as described above. Moreover, if the product is present in the form of an AAV Rep protein or as a portion thereof or as a fusion protein containing an AAV Rep protein or a portion thereof, the product may be introduced into the cells by lipofection.

The present invention provides a means to integrate foreign DNA into the genome of cells. A specific site on chromosome 19 is frequently used as a site of integration. Additionally, the tissue-specific expression of the foreign DNA is possible. Moreover, the AAV Rep protein may be provided only temporarily to the transduced cells. This may have favorable influences on the cells.

In addition, the present invention is not limited to certain cells or to certain cellular environments. The present invention can be used for transducing cells that are within an organism or outside an organism. In particular, the present invention is perfectly suited to transduce cells of a withdrawn tumor material without these cells having to be cultured beforehand.

Therefore, the present invention is suited for use in gene therapy, particularly of monogenic diseases such as hemoglobin anomalies, cystic fibrosis, subtypes of Parkinson's disease and hemophilias, AIDS and cancers.

The following example is provided to illustrate the invention. However, the invention is not limited thereby.

EXAMPLE 1

Transduction of Cells

The transduction system according to the invention that is used is one wherein components (a) and (b) are separate from each other.

(a) Cells of the human cervical carcinoma line HeLa are transfected with an expression plasmid pRc/CMV (Invitrogen) which contains an AAV-rep gene under the control of the CMV promoter. In preliminary tests using such an expression plasmid it was shown that a transfection efficiency of 30 to 60% can be achieved.

The expression of the AAV-rep gene is determined in the immunoblot by an antibody directed against AAV-Rep 78.

The transfected cells are then infected with a rep-negative AAV vector, i.e., a virus particle containing an expressible foreign DNA; e.g., a DNA coding for a B7 protein. A specific integration of the foreign DNA is obtained at chromosome 19. This is proved by common methods. Moreover, expression of the B7 protein is obtained. This is proved by an antibody directed against the B7 protein.

(b) Cells of the human cervical carcinoma line HeLa are transfected with two expression plasmids. One, pUHD15-1, codes for the fusion protein tetR-VP16 (cf. Gossen, M. et al., *PNAS USA* 89 (1992), 5547–5551). tetR is a tetracycline repressor while VP16 is the transactivation domain of the VP16 molecule of HSV. The second expression plasmid, pUHD10-3, contains an AAV-rep gene which is controlled by a promoter that is induced by the fusion protein tetR-VP16. This induction is obtained when tetracycline is removed from the medium. The detection of transfection is determined via the expression of a neomycin resistance gene on the first expression plasmid and the expression of the rep gene on the second expression plasmid.

The transfected cells are then infected with the rep-negative AAV vector of (a) containing a foreign DNA coding for a B7 protein. Having removed tetracycline from the medium, a specific integration of the foreign DNA is obtained at chromosome 19. This is proved by common methods. Moreover, an expression of the B7 protein is obtained. This is proved by an antibody directed against the B7 protein.

The above data demonstrate that a transduction system according to the invention is capable of integrating a foreign DNA specifically into the genome of cells.

The invention having been described in detail, the scope of the invention is limited only by the appended claims.

What is claimed is:

1. A transduction system comprising:

(a) a rep-negative adeno-associated virus (AAV) vector containing a foreign DNA; and (b) a product providing an AAV Rep protein, wherein the AAV vector is bound to the product, wherein said product is a protein.

2. The transduction system according to claim 1, wherein the rep-negative AAV vector is present as DNA.

3. The transduction system according to claim 1, wherein the foreign DNA is expressible.

4. The transduction system according to claim 1, wherein the foreign DNA is controlled by an inducible promoter.

5. The transduction system according to claim 1, wherein the product is a Rep-protein.

6. An in vitro method of transducing a cell comprising the step of introducing a transduction system according to claim 1.

7. The method of claim 6, wherein the cell is a healthy, diseased or tumor cell.

* * * * *